US00PP29818P2

(12) United States Plant Patent
Probst

(10) Patent No.: US PP29,818 P2
(45) Date of Patent: Nov. 6, 2018

(54) ***COREOPSIS* PLANT NAMED 'RED TAPESTRY'**

(50) Latin Name: ***Coreopsis* hybrid**
Varietal Denomination: Red Tapestry

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 15/731,179

(22) Filed: Apr. 28, 2017

(51) Int. Cl.
*A01H 5/02* (2018.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Penny J Aguirre

(57) ABSTRACT

A new cultivar of hybrid *Coreopsis* named 'Red Tapestry' that is characterized by its sturdy, well-branched plant habit reaching an average of 40 cm in height and 65 cm in width, floriferous and long blooming season of sterile inflorescences that do not require deadheading; bloom commences in early July and lasts until frost in Kensington, Conn., its medium sized inflorescences with ray florets that are dark yellow in color with red eye zones in color, its resistance to powdery mildew and leafspot, and its cold hardiness at least to U.S.D.A. Zone 5.

2 Drawing Sheets

Botanical classification: *Coreopsis* hybrid.
Variety denomination: 'Red Tapestry'.

BACKGROUND OF THE INVENTION

The present invention relates to a new and distinct cultivar of *Coreopsis* plant, botanically of hybrid origin and known as *Coreopsis* 'Red Tapestry' and will be referred to hereinafter by its cultivar name, 'Red Tapestry'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms that do not require vernalization to intiate flowering.

The Inventor made a controlled cross in August of 2013 in New Braintree, Mass. between an unnamed and unpatented plant from his breeding program, ref. no. J 06-1, as the female parent and pollen that was pooled from a variety of unnamed plants from his breeding program as the male parent. The exact characteristics of the pollen parent are therefore unknown. 'Red Tapestry' was selected in September of 2014 as a single unique plant amongst the resulting seedlings.

Asexual propagation of the new cultivar was first accomplished by stem cuttings under the direction of the Inventor in Kensington, Conn. in September of 2014. Asexual propagation by stem cutting has shown that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'Red Tapestry' as a unique cultivar of *Coreopsis*.

1. 'Red Tapestry' exhibits a sturdy, well-branched plant habit reaching an average of 40 cm in height and 65 cm in width.
2. 'Red Tapestry' exhibits a floriferous and long blooming season of sterile inflorescences that do not require deadheading; bloom commences in early July and lasts until frost in Kensington, Conn.
3. 'Red Tapestry' exhibits medium sized inflorescences with ray florets that are dark yellow in color with red eye zones.
4. 'Red Tapestry' exhibits resistance to powdery mildew and leafspot.
5. 'Red Tapestry' exhibits cold hardiness at least to U.S.D.A. Zone 5.

The female parent of 'Red Tapestry', ref. no. J 06-1, differs from 'Red Tapestry' in having a taller plant height, a floppy plant habit and inflorescences with bright yellow ray florets. 'Red Tapestry' can be most closely compared to *Coreopsis* cultivars 'Red Chiffon' (U.S. Plant Pat. No. 27,528) and 'Lightning Bug' (U.S. Plant Pat. No. 27,361). 'Red Chiffon' is similar to 'Red Tapestry' in being from a closely related breeding line, in having thread-leaf type foliage and in having similar inflorescence shape and cold hardiness. 'Red Chiffon' differs from 'Red Tapestry' in having inflorescences that are light yellow in color with red eyezones. 'Lightning Bug' is similar to 'Red Tapestry' in having inflorescences of similar size and color and in having thread-like foliage. 'Lightning Bug' differs from 'Red Tapestry' in having inflorescence with ray florets that are paler yellow in color, in being prone to powdery mildew, and in being less cold hardy.

BRIEF DESCRIPTION OF THE DRAWINGS

The accompanying colored photographs illustrate the overall appearance and distinct characteristics of the new

*Coreopsis*. The Photographs were taken of a 5 month-old plant of 'Red Tapestry' as grown outdoors in a one-gallon container from a 30-cell plug in Kensington, Conn.

Figure 1:
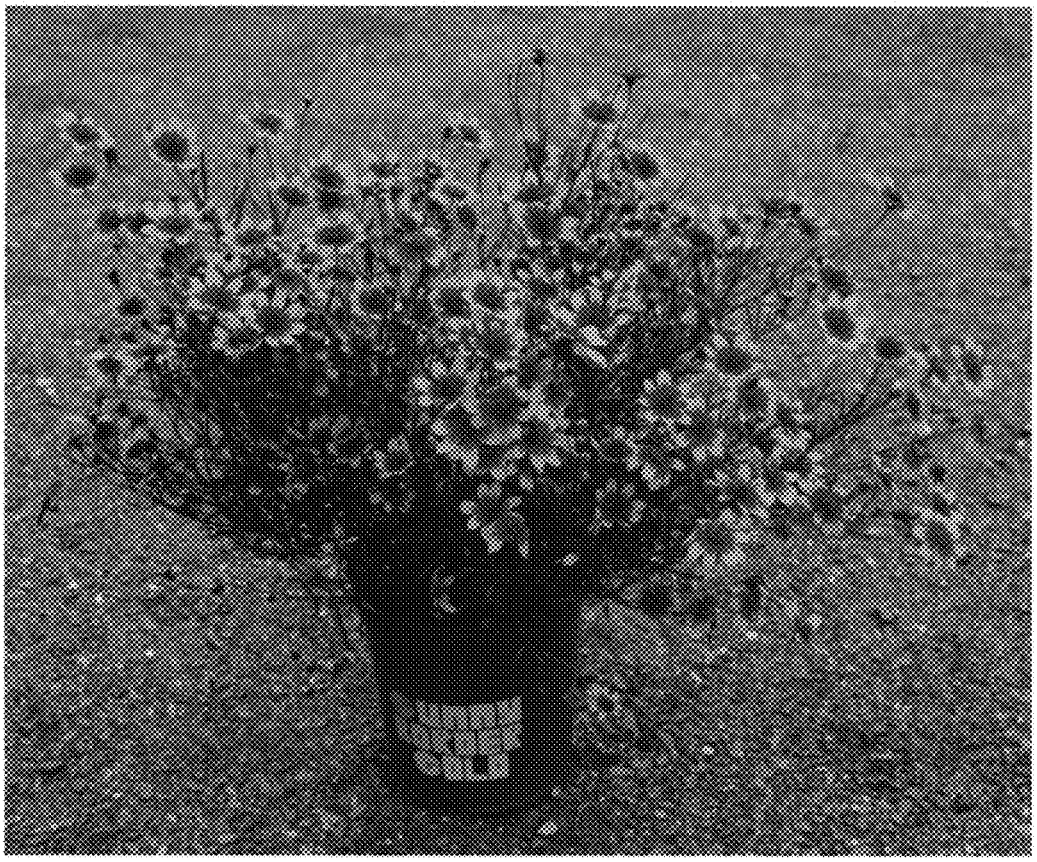

The photograph in FIG. 1 provides a side view of 'Red Tapestry' and shows the plant habit in bloom.

Figure 2:
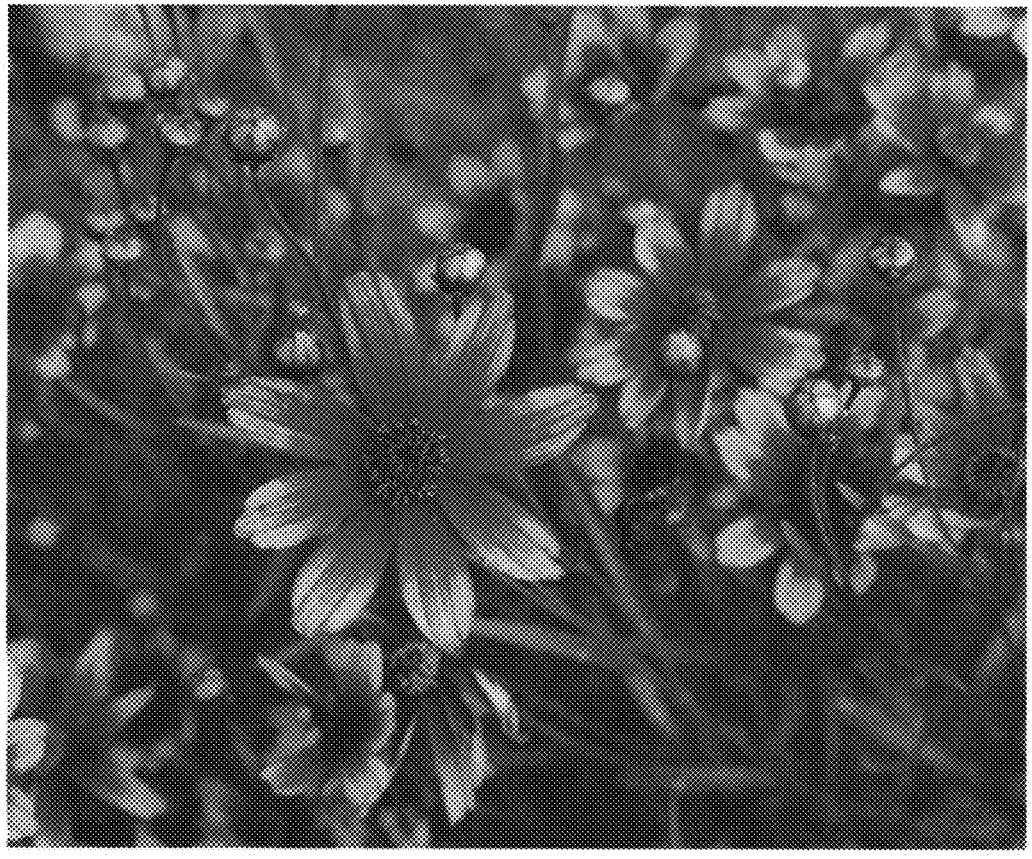

The photograph in FIG. 2 provides a close-up view of the inflorescences of 'Red Tapestry'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 5 month-old plants of 'Red Tapestry' as grown outdoors in one-gallon containers from 30-cell plugs as grown in one-gallon containers in Kensington, Conn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms from early July until frost in Kensington, Conn.

*Plant type*.—Herbaceous perennial.

*Plant habit*.—Clump-forming, compact, upright leafy flowering stems with inflorescences held above the foliage.

*Height and spread*.—An average of 40 cm in height and 65 cm in spread in the landscape.

*Cold hardiness*.—At least to U.S.D.A Zone 5a.

*Diseases and pests*.—Resistant to powdery mildew (*Podosphaera macularis*) and leaf spot (*Pseudomonas cichorii*) compared to similar varieties of *Coreopsis*.

*Root description*.—Fibrous and fine, 164C to 164D in color.

*Propagation*.—Terminal stem cuttings.

*Time required for root initiation*.—An average of 10 days.

*Growth rate*.—Moderately vigorous.

Stem description:

*Shape*.—Rounded to oval, solid.

*Stem color*.—143B.

*Stem size*.—Main stems; an average of 6.5 cm in length and 2.8 mm in width, lateral stems; an average of 15 cm in length (excluding peduncles) and 1.5 mm in width.

*Stem surface*.—Glabrous and smooth.

*Branching habit*.—Freely branched, an average of 12 basal main stems, lateral stems typically branched as oppositely arranged pairs at each node, with about 4 lateral stems (2 pairs) per main stem.

*Internode length*.—An average of 5 cm.

Foliage description:

*Leaf division*.—Simple.

*Leaf margins*.—Entire.

*Leaf size*.—An average of 5 cm in length and 5.5 mm in width.

*Leaf shape*.—Narrowly elliptic to lanceolate.

*Leaf base*.—Elongated cuneate.

*Leaf apex*.—Acute.

*Leaf venation*.—Pinnate, inconspicuous, same color as leaf.

*Leaf attachment*.—Sessile.

*Leaf arrangement*.—Opposite.

*Leaf surface*.—Upper surface satiny and glabrous, lower surfaces glabrous and dull.

*Leaf color*.—Young and mature upper surface; 137A to 137B and lower surface; 137C.

Flower description:

*Inflorescence type*.—Composite with a single row of ray florets surrounding disk florets in the center, forming a radiant head, inflorescences are borne on branch terminals in loose corymbs.

*Lastingness of inflorescence*.—About one week until senescence of ray florets, phyllaries and disk flowers are persistent.

*Fragrance*.—Faint sweet scent.

*Quantity of inflorescences*.—Free flowering, with an average of 100 inflorecenses.

*Inflorescence size*.—Corymbs; an average of 13 cm in length and 4.5 in width, composite; average of 9 mm in depth and 3.8 cm in diameter with disk portion up to 1.1 cm in diameter.

*Inflorescence buds*.—Globose in shape, an average of 6 mm in depth and diameter, smooth and glossy surface; color; 143C to 143D at the base fading to a blend between 166C and 13B suffused with 178A to 178B towards apex.

*Peduncle*.—Rounded in shape, thin and flexible, an average of 8 cm in length and 1 mm in diameter, 143B in color, smooth and glabrous surface.

Phyllaries (involucral phyllaries):

*Phyllary number*.—Two rows of 8.

*Phyllary arrangement*.—Outer phyllaries; slightly and irregularly overlapping, held upright around inner phyllaries becoming more outwardly held after ray florets drop, inner phyllaries; overlap and surround receptacle with apical portion reflexed (campanulate-like).

*Phyllary size*.—Outer phyllaries; an average of 4 mm in length and 2 mm in width, inner phyllaries; an average of 8 mm in length and 4 mm in width.

*Phyllary color*.—Upper and lower surfaces, outer phyllaries; 143A at the apex fading to 144B to 144C at the base, with margins 145C, inner phyllaries; translucent,143A to 143B at the base, fading to a mix of 13B and 168B with 178A at the margin of the apex.

*Phyllary texture*.—Outer phyllaries; glabrous and smooth on both surfaces, inner phyllaries; glabrous and waxy on both surfaces.

*Phyllary apex*.—Acute.

*Phyllary base*.—Truncate.

*Phyllary shape*.—Outer phyllaries; lanceolate, inner phyllaries; ovate to lanceolate.

Ray florets (no reproductive organs):

*Number*.—8.

*Shape*.—Oblanceolate, with the appearance of 3 longitudinal sections.

*Size*.—An average of 1.7 cm in length and 7 mm in width.

*Apex*.—Rounded with three rounded lobes.
*Base*.—Broadly cuneate.
*Margins*.—Entire on sides with lobed apex.
*Aspect*.—Held horizontal, perpendicular to peduncle, to slightly upwards.
*Texture*.—Both surfaces; glabrous, dull, and satiny.
*Color*.—Upper surface when opening and when fully open; 42A at eye zone with the outer region predominantly 13A lightly suffused with 42A at the apex, lower surface when opening and when fully open; 13B with 42A at the base.

Disk florets (male and female):
*Number*.—An average of 60.
*Shape*.—Tubular, corolla is fused, flared at apex.
*Size*.—About 8.2 mm in length and 1 mm in width.
*Color*.—En masse; a mix between 17A and 183B, corolla; base (tube) transluscent 13B and flared portion 183A.
*Receptacle*.—An average of 4 mm in diameter and 1 mm in depth, 143C in color.

Reproductive organs:
*Presence*.—Disk flowers only.
*Gynoecium*.—1 Pistil, an average of 5 mm in length, style is very fine and transluscent 13C with 150C at the base in color, bifid pillose stigma is 17A in color with recurved branches about 0.4 mm in length, ovary is inferior, oblong in shape, an average of 2 mm in length and 1.mm in width, and 1C in color.
*Androcoecium*.—4 stamens, fused into tube surrounding style, an average of 2 mm in length and 0.7 mm in width, 200A in color, pollen; moderately abundant in quantity, 17A in color.
*Seed*.—No seed development was observed, have been observed to be sterile.

It is claimed:

1. A new and distinct cultivar of *Coreopsis* plant named 'Red Tapestry' as herein illustrated and described.

* * * * *